(12) United States Patent
Mine

(10) Patent No.: US 12,243,350 B2
(45) Date of Patent: Mar. 4, 2025

(54) ELECTRONIC APPARATUS, CONTROL METHOD OF ELECTRONIC APPARATUS, AND NON-TRANSITORY COMPUTER READABLE MEDIUM

(71) Applicant: CANON KABUSHIKI KAISHA, Tokyo (JP)

(72) Inventor: Yosuke Mine, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 60 days.

(21) Appl. No.: 18/300,684

(22) Filed: Apr. 14, 2023

(65) Prior Publication Data

US 2023/0343139 A1  Oct. 26, 2023

(30) Foreign Application Priority Data

Apr. 20, 2022 (JP) .................................. 2022-069647

(51) Int. Cl.
  *G06V 40/18* (2022.01)
  *G06F 3/01* (2006.01)
  *G06V 10/141* (2022.01)
  *G06V 10/60* (2022.01)
  *G06V 10/74* (2022.01)

(52) U.S. Cl.
  CPC ............ *G06V 40/18* (2022.01); *G06F 3/013* (2013.01); *G06V 10/141* (2022.01); *G06V 10/60* (2022.01); *G06V 10/761* (2022.01)

(58) Field of Classification Search
  None
  See application file for complete search history.

(56) References Cited

U.S. PATENT DOCUMENTS

| | | | |
|---|---|---|---|
| 2009/0226158 A1* | 9/2009 | Omoto | B60R 21/01538 396/61 |
| 2011/0228163 A1* | 9/2011 | Isaka | H04N 25/531 348/E5.022 |
| 2013/0242073 A1 | 9/2013 | Watanabe | |
| 2016/0255261 A1 | 9/2016 | Govari | |
| 2017/0251366 A1* | 8/2017 | Perna | G06F 21/32 |

(Continued)

FOREIGN PATENT DOCUMENTS

| | | |
|---|---|---|
| JP | 61-172552 A | 8/1986 |
| JP | 04-347132 A | 12/1992 |

(Continued)

OTHER PUBLICATIONS

The above patent documents were cited in a European Search Report issued on Oct. 20, 2023, which is enclosed, that issued in the corresponding European Patent Application No. 23165888.1.

*Primary Examiner* — Eileen M Adams
(74) *Attorney, Agent, or Firm* — Cowan, Liebowitz & Latman, P.C.

(57) ABSTRACT

An electronic apparatus according to the present invention includes at least one memory and at least one processor which function as: a first acquisition unit configured to acquire an image of an eyeball illuminated by a plurality of light sources and captured by an image sensor; a second acquisition unit configured to acquire distance information that indicates a distance from the eyeball to the image sensor; and a correction unit configured to correct brightness unevenness of the image with a correction amount in accordance with the distance information.

12 Claims, 14 Drawing Sheets

(56) References Cited

U.S. PATENT DOCUMENTS

| | | | |
|---|---|---|---|
| 2018/0220887 A1* | 8/2018 | Kanamori | A61B 3/12 |
| 2020/0236255 A1 | 7/2020 | Takahashi | |
| 2020/0327323 A1* | 10/2020 | Noble | G06T 7/20 |
| 2022/0092815 A1* | 3/2022 | Iizuka | B66F 9/24 |

FOREIGN PATENT DOCUMENTS

| | | |
|---|---|---|
| JP | 2017124153 A | 7/2017 |
| JP | 2018181025 A | 11/2018 |
| JP | 2020140637 A | 9/2020 |

* cited by examiner

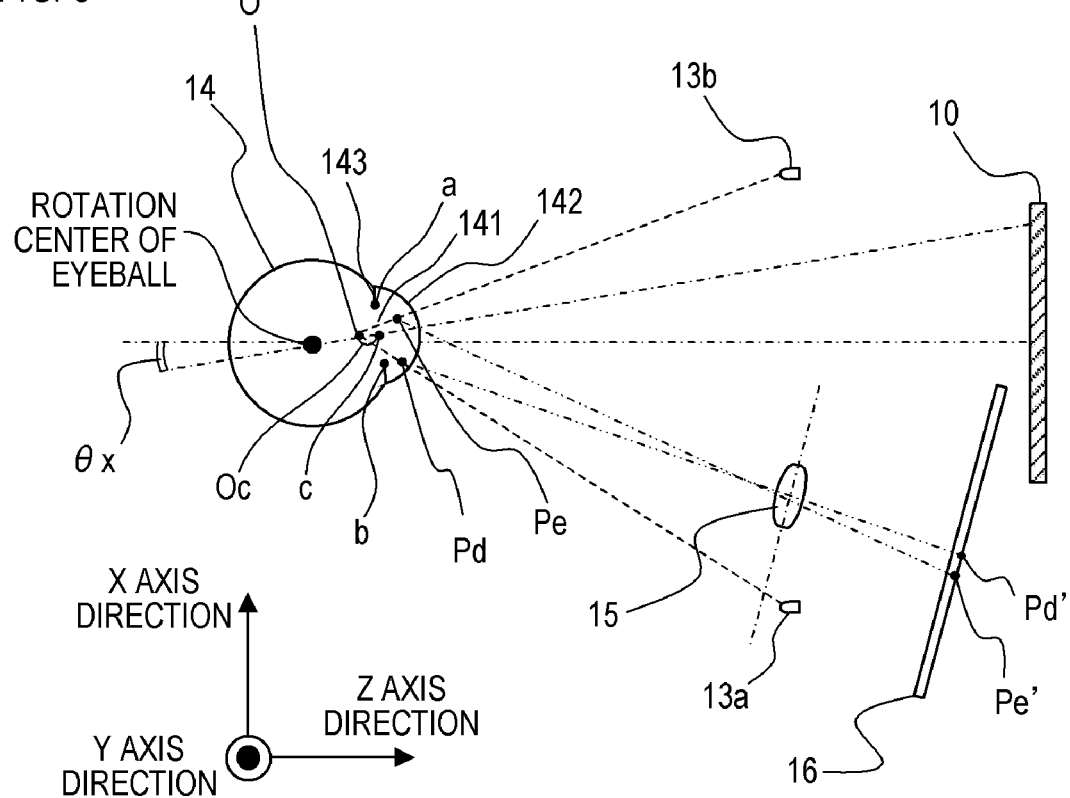

ELECTRONIC APPARATUS, CONTROL METHOD OF ELECTRONIC APPARATUS, AND NON-TRANSITORY COMPUTER READABLE MEDIUM

BACKGROUND OF THE INVENTION

Field of the Invention

The present invention relates to an electronic apparatus, a control method of electronic apparatus, and a non-transitory computer readable medium.

Description of the Related Art

Methods for detecting which position a user (observer) is observing on an observation surface have been proposed. For example, according to a technique disclosed in Japanese Patent Application Publication No. S61-172552, parallel beams are projected from a plurality of light sources to the cornea (anterior ocular segment) of an eyeball of the user, and the line-of-sight is detected using the positional relationship between a corneal reflex image formed by the reflected light from the corner and the center of a pupil. According to a technique disclosed in Japanese Patent Application Publication No. H04-347132, a pupil circle is estimated based on the coordinates of a corneal reflex image in the horizontal/vertical directions, and the center coordinates of the pupil circle are used for detecting the line-of-sight.

However, with the technique disclosed in Japanese Patent Application Publication No. S61-172552 or Japanese Patent Application Publication No. H04-347132, notable brightness unevenness is generated in an eye image (captured image of an eyeball of the user) in a case where the distance from the plurality of light sources to the eyeball is short, compared with the case where this distance is long. In particular, the brightness unevenness is more noticeably generated in a configuration where a light-receiving lens and an area sensor are disposed outside an eyepiece.

SUMMARY OF THE INVENTION

With the foregoing in view, the present invention provides a technique for suppressing the brightness unevenness of a captured image of an eyeball.

The present invention in its first aspect provides an electronic apparatus including at least one memory and at least one processor which function as: a first acquisition unit configured to acquire an image of an eyeball illuminated by a plurality of light sources and captured by an image sensor; a second acquisition unit configured to acquire distance information that indicates a distance from the eyeball to the image sensor; and a correction unit configured to correct brightness unevenness of the image with a correction amount in accordance with the distance information. The present invention in its second aspect provides an electronic apparatus including: a plurality of light sources configured to illuminate an eyeball; an image sensor configured to capture the eyeball illuminated by the plurality of light sources; and at least one memory and at least one processor which function as a control unit configured to control the plurality of light sources, wherein the control unit controls the plurality of light sources so as to emit light at a light-emitting amount based on a positional relationship between each of the plurality of light sources and the image sensor. The present invention in its third aspect provides an electronic apparatus including at least one memory and at least one processor which function as a control unit configured to control such that brightness unevenness of a first image is approximately the same as brightness unevenness of a second image, the first image being an image of an eyeball acquired in a case where a distance from the eyeball to an image sensor that captures the eyeball is a first distance, and the second image being an image of the eyeball acquired in a case where the distance is a second distance which is longer than the first distance.

The present invention in its fourth aspect provides a control method of an electronic apparatus, including: acquiring an image of an eyeball illuminated by a plurality of light sources and captured by an image sensor; acquiring distance information that indicates a distance from the eyeball to the image sensor; and correcting brightness unevenness of the image with a correction amount in accordance with the distance information. The present invention in its fifth aspect provides a control method of an electronic apparatus, including: capturing an eyeball illuminated by a plurality of light sources with an image sensor; and controlling the plurality of light sources, wherein the plurality of light sources are controlled so as to emit light at a light-emitting amount based on a positional relationship between each of the plurality of light sources and the image sensor.

The present invention in its sixth aspect provides a non-transitory computer readable medium that stores a program, wherein the program causes a computer to execute the above described control method.

Further features of the present invention will become apparent from the following description of exemplary embodiments with reference to the attached drawings.

BRIEF DESCRIPTION OF THE DRAWINGS

FIG. 3 is a diagram for describing a principle of a line-of-sight detection method according to Embodiment 1;

DESCRIPTION OF THE EMBODIMENTS

Embodiments of the present invention will now be described with reference to the drawings.

Embodiment 1

Configuration

Figure 1:
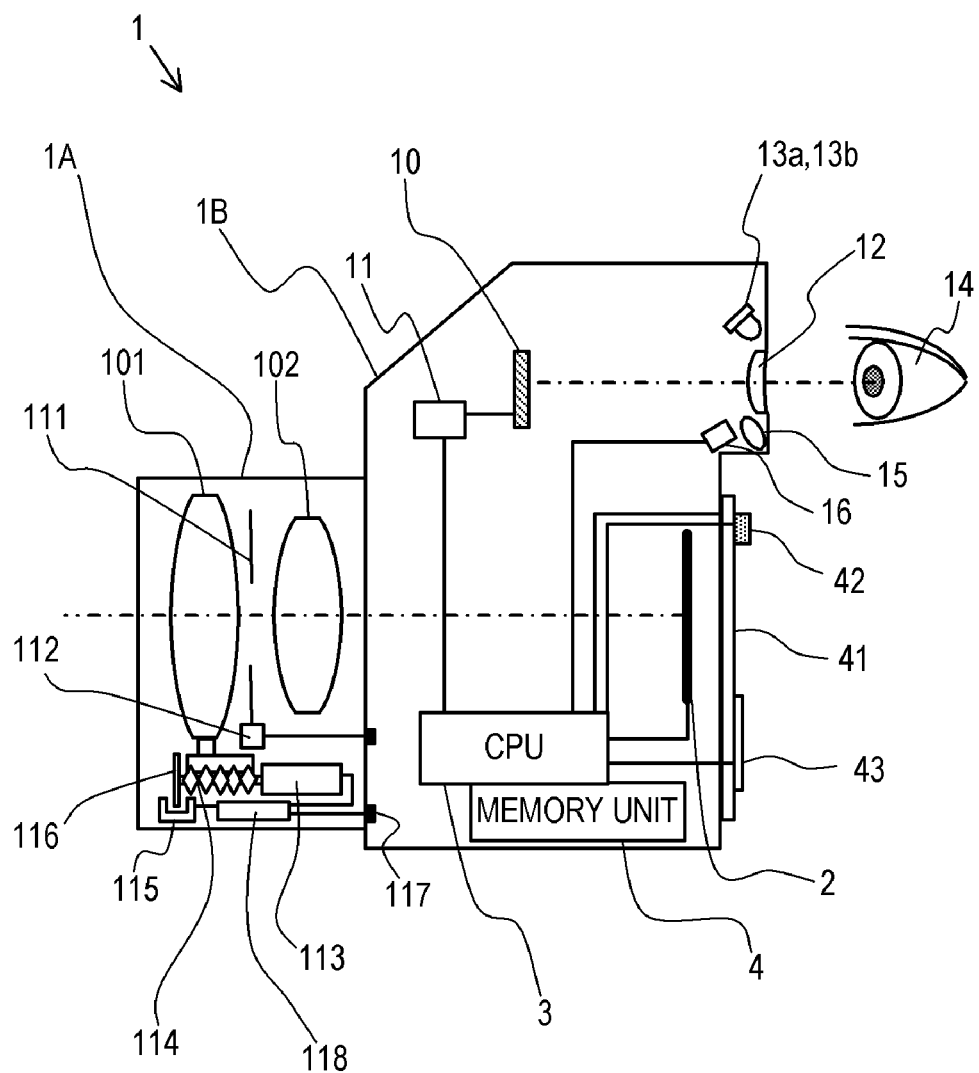
FIG. 1 is a cross-sectional view of a camera according to Embodiment 1.

FIG. 1 is a cross-sectional view of a camera 1 (imaging apparatus; electronic apparatus), and indicates a general internal configuration of the camera 1. Inside an image capturing lens unit 1A, two lenses 101, 102, an aperture 111, an aperture driving unit 112, a lens driving motor 113, a lens driving member 114, a photocoupler 115, a pulse plate 116, a mount contact 117, a focus adjustment circuit 118, and the like are included. The lens driving member 114 is constituted of a driving gear and the like, and the photocoupler 115 detects a rotation of the pulse plate 116 interlocking with the lens driving member 114, and transfers this detection to the focus adjustment circuit 118. Based on information from the photocoupler 115 and information from a camera housing 1B (information on lens driving amount), the focus adjustment circuit 118 drives the lens driving motor 113, so as to move the lens 101 and change the focus position. The mount contact 117 is an interface between the image capturing lens unit 1A and the camera housing 1B. For simplicity, two lenses 101 and 102 are illustrated, but more than two lenses are actually included in the image capturing lens unit 1A.

In the camera housing 1B, an image pickup element 2 (imaging unit, image sensor), a CPU 3, a memory unit 4, a display device 10, a display device driving circuit 11, and the like are included. The image pickup element 2 is disposed on a planned image forming surface of the image capturing lens unit 1A. The CPU 3 is a central processing unit of a microcomputer, and controls the entire camera 1. The memory unit 4 stores images captured by the image pickup element 2 and the like. The display device 10 is constituted of liquid crystals and the like, and displays a captured image (object image) and the like on a screen (display surface) of the display device 10. The display device driving circuit 11 drives the display device 10. The user can view the screen of the display device 10 via the eyepiece 12.

In the camera housing 1B, light sources 13a and 13b, a light-receiving lens 15, an eye image pickup element 16, and the like are also included. The light sources 13a and 13b are light sources which are conventionally used for a single lens reflex camera or the like, to detect a line-of-sight (gaze) direction based on the relationship between a reflex image (corneal reflex image), generated by the corneal reflex of light, and a pupil, and are light sources to illuminate an eyeball 14 of the user. Specifically, the light sources 13a and 13b are infrared light-emitting diodes that emit infrared light invisible to the user, for example, and are disposed around the eyepiece 12. An optical image of the illuminated eyeball 14 (eyeball image; an image generated by the reflex lights which were emitted from each light source 13a and 13b and is reflected by the eyeball 14) transmits through the eyepiece 12, and forms an image on the eye image pickup element 16, where rows of such photoelectric elements as CCDs are two-dimensionally disposed, by the light-receiving lens 15. The light-receiving lens 15 is positioned so that the pupil of the eyeball 14 and the eye image pickup element 16 are in a conjugated image forming relationship. Based on the later mentioned predetermined algorithm, the line-of-sight direction of the eyeball 14 (line-of-sight position; view point on the screen of the display device 10) is detected from the position of the corneal reflex image in the eyeball image formed on the eye image pickup element 16. Operation members 41 to 43, which receive various operations performed by the user, are also disposed on the rear face of the camera housing 1B.

Figure 2:
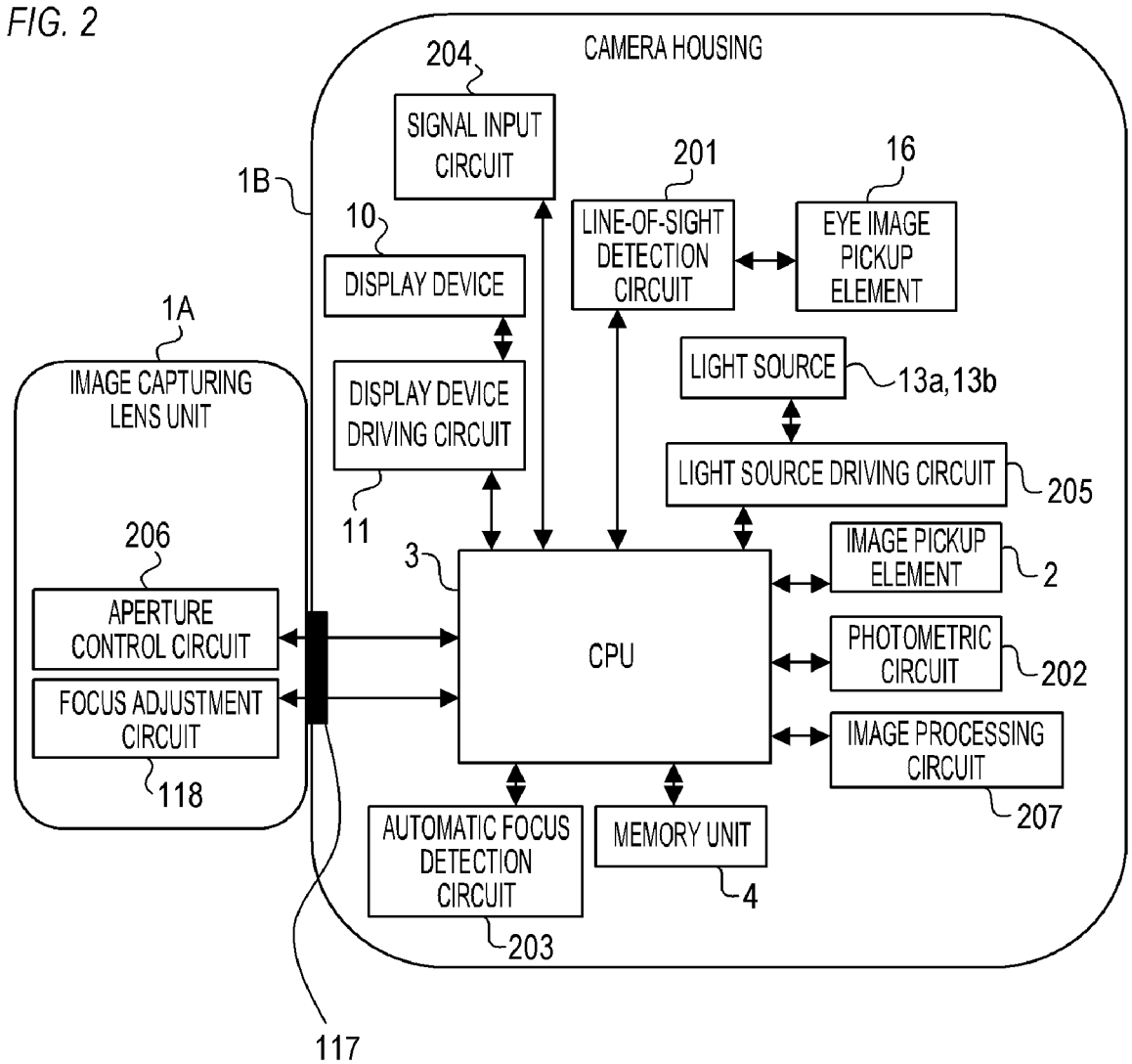
FIG. 2 is a block diagram of the camera according to Embodiment 1.

FIG. 2 is a block diagram depicting an electric configuration inside the camera 1. To the CPU 3, a line-of-sight detection circuit 201, a photometric circuit 202, an automatic focus detection circuit 203, a signal input circuit 204, the display device driving circuit 11, a light source driving circuit 205, and the like are connected. The CPU 3 transfers signals to the focus adjustment circuit 118 disposed inside the image capturing lens unit 1A, and an aperture control circuit 206 included in the aperture driving unit 112 inside the image capturing lens unit 1A, via the mount contact 117. The memory unit 4 attached to the CPU 3 has a function to store imaging signals from the image pickup element 2 and the eye image pickup element 16.

The line-of-sight detection circuit 201 performs A/D conversion on the output (eye image capturing an eye) of the eye image pickup element 16 (CCD-EYE) in a state where an eyeball image is formed on the eye image pickup element 16, and sends the result to the CPU 3. The CPU 3 extracts feature points required for detecting the line-of-sight from the eye image, in accordance with the later mentioned predetermined algorithm, and calculates the line-of-sight (viewpoint on the screen of the display device 10) of the user based on the positions of the feature points.

The photometric circuit 202 performs amplification, logarithmic compression, A/D conversion and the like on a signal acquired from the image pickup element 2, which plays a role of a photometric sensor as well, (specifically, on a brightness signal corresponding to the brightness of a field), and sends the result to the CPU 3 as the field brightness information.

The automatic focus detection circuit 203 performs A/D conversion on a signal voltage from a plurality of detection elements (a plurality of pixels) which are included in the CCDs in the image pickup element 2 and are used for phase difference detection, and sends the result to the CPU 3. Based on the signals from the plurality of detection elements, the CPU 3 computes a distance to an object corresponding to each focus detection point. This is a publicly known technique known as the image plane phase difference AF. In Embodiment, 1 for example, it is assumed that a focus detection point exists in each of the 180 locations on the imaging plane, which correspond to 180 locations on the visual field image in the finder (screen of the display device 10).

To the signal input circuit 204, a switch SW1, which turns ON by the first stroke of the release button and starts photometry, distance measurement, line-of-sight detection operation, and the like for the camera 1, and a switch SW2, which turns ON by the second stroke of the release button and starts image capturing operation, are connected. ON signals from the switches SW1 and SW2 are inputted to the signal input circuit 204, and are sent to the CPU 3.

The light source driving circuit 205 drives the light sources 13a and 13b.

The image processing circuit 207 applies predetermined image processing to image data, so as to generate signals and image data, and to acquire and/or generate various information. For example, the image processing circuit 207 may be a dedicated hardware circuit, such as ASIC, that is designed to implement a specific function, or a processor such as DSP may be configured to implement a specific function by executing software.

The image processing that the image processing circuit 207 applies includes pre-processing, color interpolation processing, correction processing, detection processing and data processing. The pre-processing includes signal amplification, reference level adjustment and defective pixel correction. The color interpolation processing is processing to interpolate values of color components that are not included in the image data, and is also called "demosaicing". The correction processing includes white balance adjustment, processing to correct brightness of the image, processing to correct optical aberration of the image capturing lens unit 1A, and processing to correct colors. The detection processing includes detection of a feature region (e.g. face region, human body region, object region), tracking processing and person recognition processing. The data processing includes scaling processing, encoding/decoding, and header information generation processing. These are merely examples of image processing that the image processing circuit 207 can execute, and are not intended to limit image processing executed by the image processing circuit 207.

Principle of Line-of-Sight Detection Operation

A principle of the line-of-sight detection operation will be described next, with reference to FIGS. 3, 4A and 4B. FIG. 3 is a diagram for describing the principle of the line-of-sight detection method, and is a schematic diagram of an optical system to detect line-of-sight. As illustrated in FIG. 3, the light sources 13a and 13b are disposed to be approximately symmetric with respect to the optical axis of the light-receiving lens 15, and illuminate the eyeball 14 of the user. A part of the lights, emitted from the light sources 13a and 13b and reflected by the eyeball 14, is collected by the light-receiving lens 15 to the eye image pickup element 16.

Figure 4A:
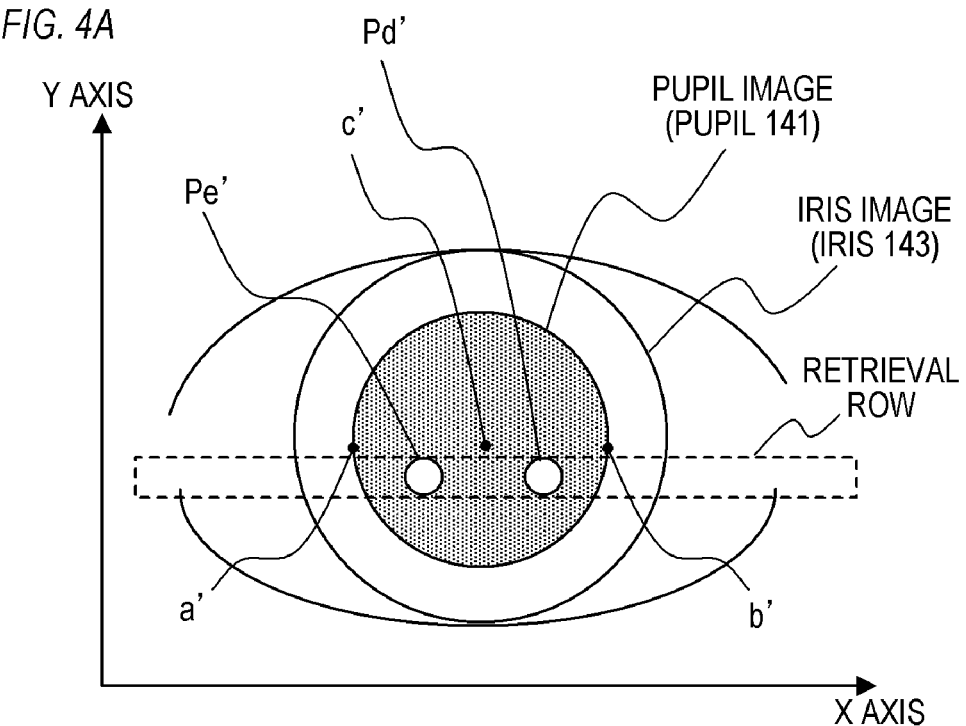
FIG. 4A is a diagram indicating an eye image according to Embodiment 1.

FIG. 4A is a schematic diagram of an eye image captured by the eye image pickup element 16 (eyeball image projected to the eye image pickup element 16). Corneal reflex images Pd and Pe of the light sources 13a and 13b and a pupil center c are detected from the eye image, and a rotation angle θx of the eyeball 14 is calculated. Then the line-of-sight position of the user (observer) on the display device 10 is calculated based on the rotation angle θx and the calibration data.

First the method for detecting the corneal reflex images Pd and Pe will be described. In FIG. 4A, the X axis indicates the horizontal direction of the eye image, and the Y axis indicates the vertical direction of the eye image. Here the corneal reflex images Pd and Pe of the light sources 13a and 13b are collected by the light-receiving lens 15, form images on the eye image pickup element 16, and becomes the corneal reflex images Pd' and Pe' in the eye image. The coordinates of the corneal reflex image Pd' are assumed to be (Xd, Yd), and the coordinates of the corneal reflex image Pe' are assumed to be (Xe, Ye). In the same manner, the luminous flux from the edges a and b of the pupil 141 form images on the eye image pickup element 16, and become the pupil edge images a' and b' in the eye image. The coordinates of the pupil edge image a' are assumed to be (Xa, Ya), and the coordinates of the pupil edge image b' are assumed to be (Xb, Yb). The luminous flux from the pupil center c forms an image on the eye image pickup element 16, and becomes a pupil center image c'.

Figure 4B:
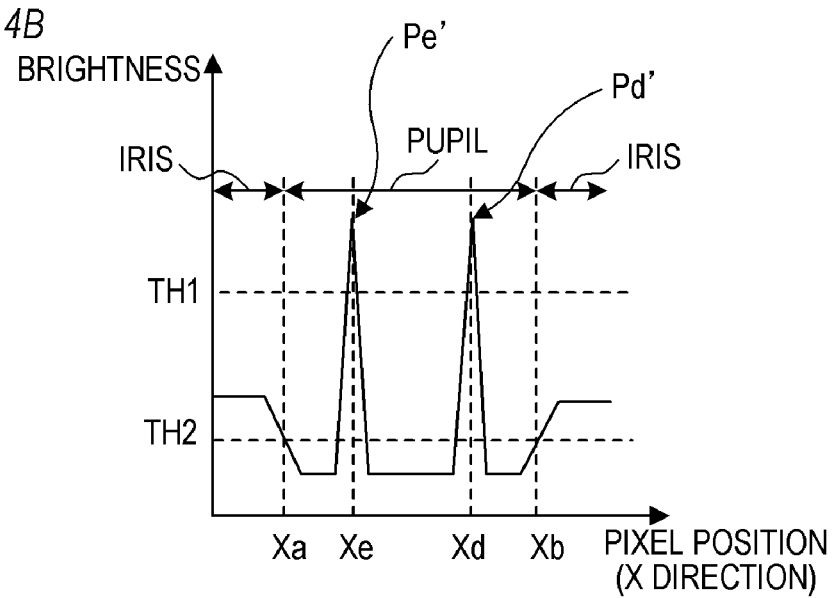
FIG. 4B is a graph indicating brightness distribution of the eye image according to Embodiment 1.

FIG. 4B indicates the brightness information (brightness distribution) of one arbitrary row (hereafter called "retrieval row") in the eye image in FIG. 4A. As indicated in FIG. 4B, brightness, of which level is extremely strong (brightness threshold TH1 or more), is acquired in the corneal reflex images Pd' and Pe'. By sequentially determining the brightness level while changing the retrieval row, coordinates, where the brightness becomes the brightness threshold TH1 or more, can be detected in the entire eye image. Thereby two regions, where the brightness is the brightness threshold TH1 or more, are detected. By computing the gravity centers of the two regions respectively, the coordinates (Xd, Yd) of the corneal reflex image Pd' and the coordinates (Xe, Ye) of the corneal reflex image Pe' can be acquired.

The method for detecting the center (contour center) c of the pupil 141 will be described next. In FIG. 4B, the coordinates of the pupil contour portions (pupil edges) are assumed to be (Xa, Ya) and (Xb, Yb). In the portion corresponding to the region of the pupil 141, brightness of which level is low (brightness threshold TH2 or less) is acquired except for the positions of the coordinates (Xd, Yd) and (Xe, Ye). Whereas in the portion corresponding to a region of an iris 143 which is on the outer side of the pupil 141, brightness of which level is relatively high (between the brightness threshold TH1 and the brightness threshold TH2) is acquired. In other words, the coordinates (Xa, Ya) and (Xb, Yb), where the brightness level changes from the brightness level between the brightness threshold TH1 and the brightness threshold TH2 to the brightness level that is the brightness threshold TH2 or less, are determined as the pupil contour portions. By sequentially determining the level of the brightness while changing the retrieval row, the contour coordinates of the pupil 141 can be detected for the entire eye image. Here the plurality of contour coordinates of the pupil 141 are also called a "contour coordinate group" of the pupil 141. The detection of the contour coordinates of the pupil 141 is also called a "contour detection".

By the circle approximation method using the contour coordinates of the pupil 141, the coordinates of the center c of the pupil 141 and the radius r of the pupil 141 are computed. Here it is assumed that the contour coordinates exist at 20 locations, and if the contour coordinates are (Xi, Yi) (where i=1 to 20), the coordinates (X0, Y0) of the center c of the pupil 141 and the radius r are calculated using the following Expression 1.

[Math 1]

$$\begin{pmatrix} \alpha \\ \beta \\ \gamma \end{pmatrix} = \begin{pmatrix} \sum Xi^2 & \sum XiYi & \sum Xi \\ \sum XiYi & \sum Yi^2 & \sum Yi \\ \sum Xi & \sum Yi & \sum 1 \end{pmatrix}^{-1} \begin{pmatrix} -\sum (Xi^3 + XiYi^2) \\ -\sum (Xi^2 Yi + Yi^3) \\ -\sum (Xi^2 + Yi^2) \end{pmatrix}$$ (Expression 1)

$$X_0 = -\frac{\alpha}{2}$$

$$Y_0 = -\frac{\beta}{2}$$

$$\gamma = \sqrt{X_0^2 + Y_0^2 - \gamma}$$

A method for calculating an image forming magnification of the eyeball image will be described next. The image forming magnification is a magnification determined by the position of the eyeball 14 with respect to the light-receiving lens 15, and can be determined using the function of the interval (Xd-Xe) of the corneal reflex images Pd' and Pe'.

The coordinates of the mid-point between the corneal reflex image Pd' and the corneal reflex image Pe' approximately match with the coordinates of the curvature center O of the cornea 142. Therefore if a standard distance from the curvature center O of the cornea 142 to the center c of the pupil 141 is Oc, the rotation angle θx of the eyeball 14 on the Z-X plane (plane vertical to the Y axis) with respect to the optical axis of the eyeball 14 can be calculated by the following Expression 2. The rotation angle θy of the eyeball 14 on the Z-Y plane (plane vertical to the X axis) can also be calculated by a method similar to the method for calculating the rotation angle θx.

$$\beta \times Oc \times \text{SIN } \theta x \approx \{(Xd+X)/2\}X0 \quad \text{(Expression 2)}$$

Using the calculated rotation angles θx and θy, the viewpoint of the user (position to which the line-of-sight is directed; position at which user is looking) on the screen of the display device 10 is determined (estimated). If the coordinates corresponding to the center c of the pupil 141 is the line-of-sight position (coordinates of the viewpoint) (Hx, Hy), then the line-of-sight position (Hx, Hy) can be calculated using the following Expressions 3 and 4.

$$Hx=m \times (\theta x - \theta x\_cal) \quad \text{(Expression 3)}$$

$$Hy=m \times (\theta y - \theta y\_cal) \quad \text{(Expression 4)}$$

The parameter m in Expression 3 and 4 is a constant that is determined by the configuration of the finder optical system (e.g. light-receiving lens 15) of the camera 1, and is a conversion coefficient to convert the rotation angles θx and θy into the coordinates corresponding to the center c of the pupil 141 on the screen of the display device 10. The parameter m is predetermined and stored in the memory unit 4 in advance. The parameters (correction values) θx_cal and θy_cal are line-of-sight correction parameters to correct the difference of the line-of-sight depending on the person, and are acquired by the calibration operation described later. The parameters θx_cal and θy_cal are stored in the memory unit 4 before the line-of-sight detection operation starts.

The calibration operation is an operation to acquire an offset amount to reduce positional deviation between the position where the user (photographer) is actually gazing and the calculated line-of-sight position (positional deviation generated due to such causes as the difference in eyeball shape depending on the person). When the calibration operation is performed, an image for calibration is displayed on the display device 10. The target frame for the user to gaze at is displayed at the center portion of the image for calibration. The rotation angles θx_cal and θy_cal for the calibration operation are acquired and stored in the memory unit 4 as the offset amounts (correction values). In the calibration operation, the accuracy of detecting the line-of-sight position can be improved by displaying the target frame at a plurality of positions, and interpolating the position between the plurality of positions using the rotation angle of each of the plurality of positions. The above is the description on the principle of the line-of-sight detection operation.

Generation Principle of Brightness Unevenness of Eye Image and Suppression Method A generation principle of brightness unevenness of an eye image and suppression method thereof will be described next with reference to FIGS. 5A, 5B, 6A, 6B, 7A, 7B and 8A to 8C.

Figure 5A:
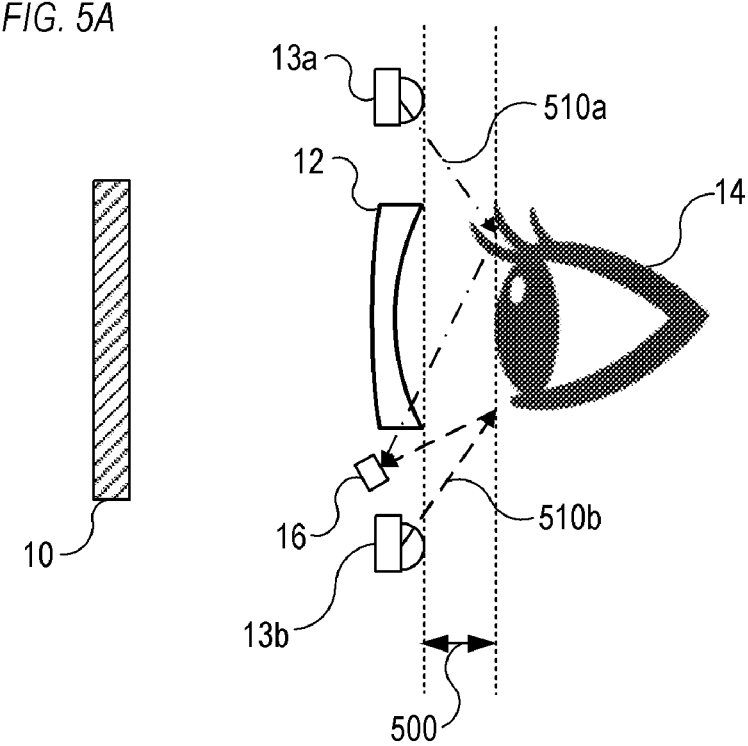
FIGS. 5A and 5B are diagrams indicating a generation principle of brightness unevenness of the eye image according to Embodiment 1.
Figure 5B:
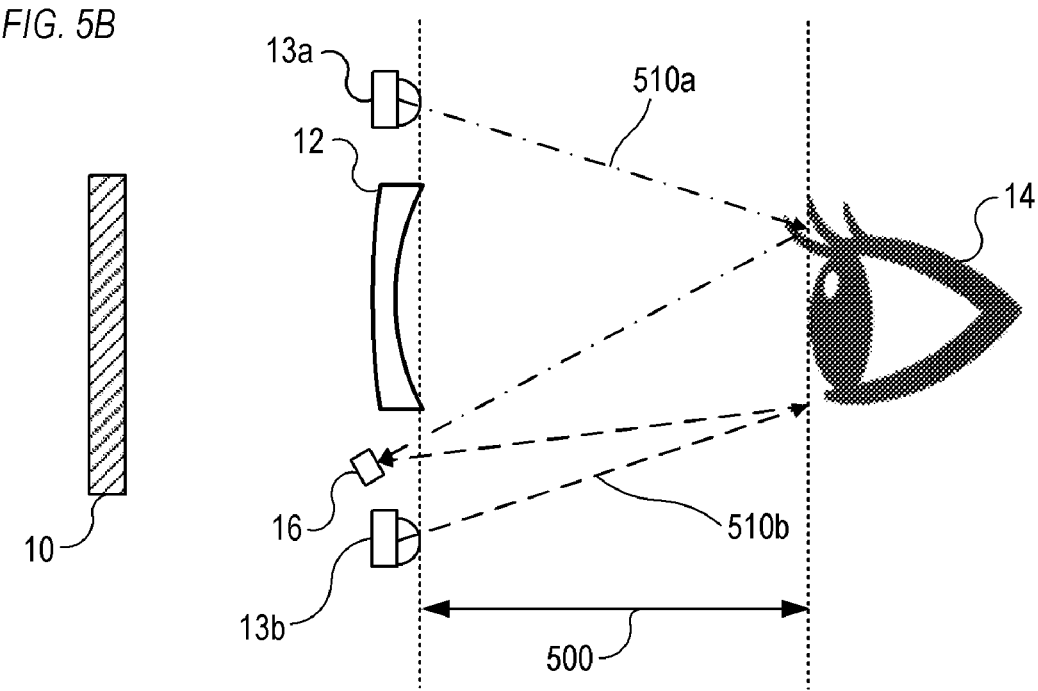

FIGS. 5A and 5B are diagrams indicating the generation principle of the brightness unevenness. In FIGS. 5A and 5B, the light sources 13a and 13b illuminate the eyeball 14, just like FIG. 3. Here the user is looking at an image displayed on the display device 10. A part of the light reflected by the eyeball 14 of the user is collected on the eye image pickup element 16. An eye point distance (distance from the eyepiece 12 to the eyeball 14) 500 in FIG. 5B is longer than an eye point distance 500 in FIG. 5A. Beams 510a and 510b indicate optical paths when each light reflected from a region (area), where the light sources 13a or 13b is mainly illuminating, reaches the eye image pickup element 16.

Figure 6A:
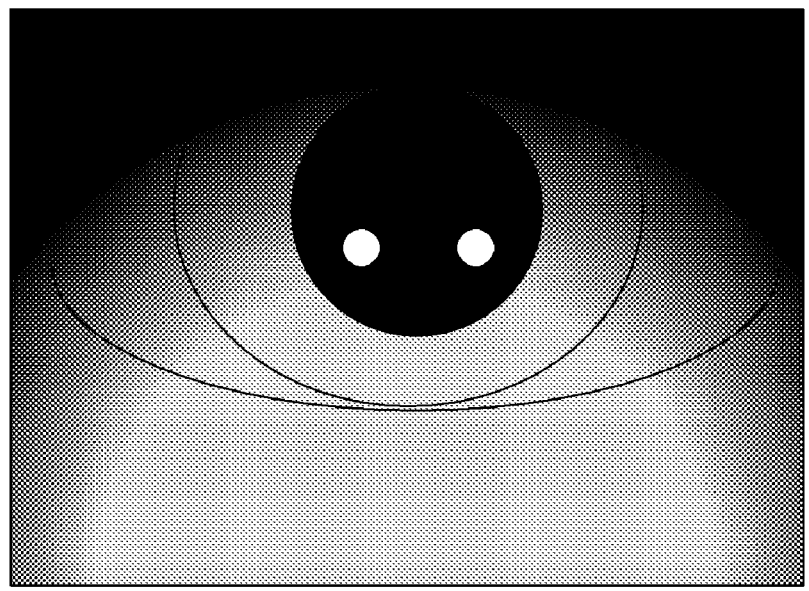
FIGS. 6A and 6B are diagrams for describing the brightness unevenness according to Embodiment 1.
Figure 6B:
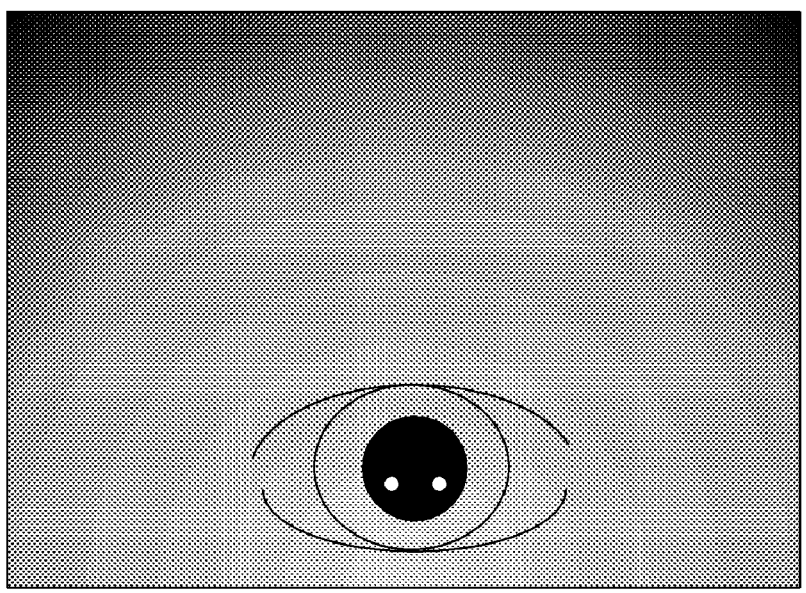

FIG. 6A is a diagram for describing the brightness unevenness of the eye image captured by the eye image pickup element 16 with the eye point distance 500 indicated in FIG. 5A. FIG. 6B is a diagram for describing the brightness unevenness of the eye image captured by the eye image pickup element 16 with the eye point distance 500 indicated in FIG. 5B. In the eye image in FIG. 6A, brightness unevenness, where a lower portion of the screen is bright and upper portion of the screen is dark, is generated. The brightness unevenness indicated in FIG. 6A is generated when the quantities of light of the regions where the light sources 13a and 13b are mainly illuminated are in inverse proportion to the square of the distances of the beams 510a and 510b respectively. The brightness unevenness of the eye image in FIG. 6B is smaller than the brightness unevenness of the eye image in FIG. 6A because the distance between the beams 510a and 510b in FIG. 5B is smaller than the difference between the beams 510a and 510b in FIG. 5A.

In the case where the lines-of-sight detection operation indicated in FIG. 4B is performed using the image where the brightness unevenness is generated, it becomes difficult to detect the coordinates (Xa, Ya) and (Xb, Yb) of the contour portion of the pupil. As number of contour coordinates of the pupil to be detected decreases, the results of computing the coordinates (X0, Y0) of the center c of the pupil and the radius r of the pupil based on the circle approximation method deteriorate as well. As the computing results deteriorate, line-of-sight detection errors (failure of line-of-sight detection; increasing viewpoint detection errors) are likely to be generated, and in some cases, appropriate focus detection and adjustment may not be performed. There is a method for changing the brightness threshold TH2 within the image in accordance with the eye point distance, but in this case, a computing volume becomes large.

Figure 7A:
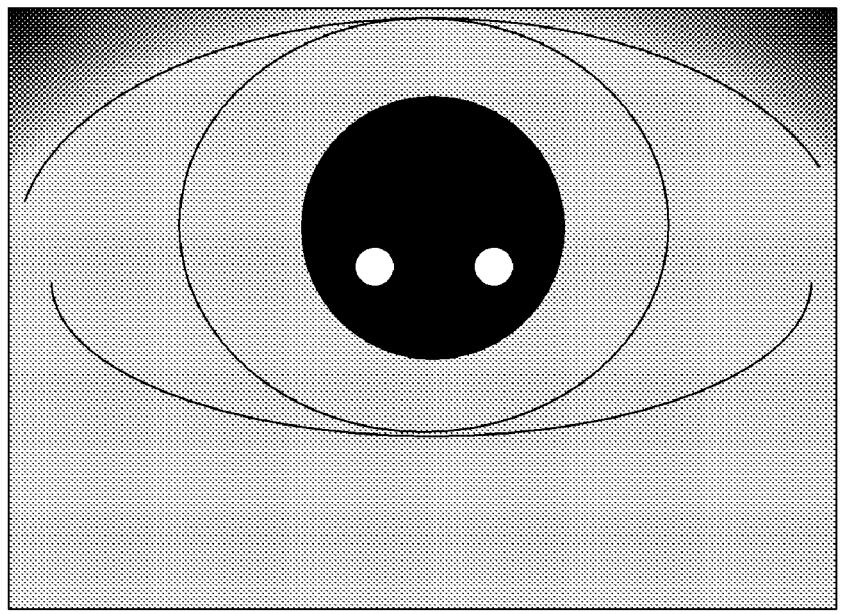
FIGS. 7A and 7B are diagrams of eye images when brightness unevenness is suppressed according to Embodiment 1.
Figure 7B:
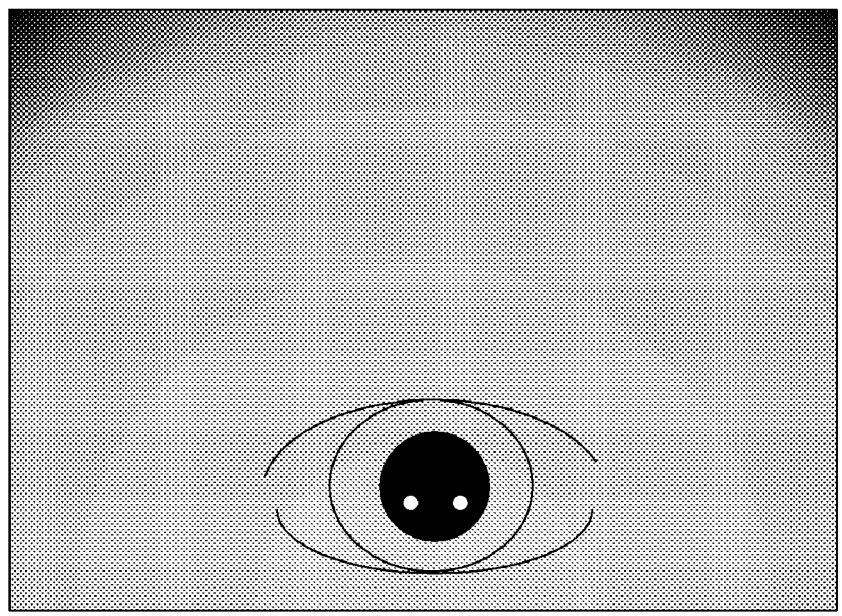

Therefore in a first method for suppressing the brightness unevenness, the CPU 3 of the camera 1 performs shading correction using a correction value (correction amount) in accordance with the eye point distance, for the eye image in which the brightness unevenness is generated. FIGS. 7A and 7B are eye images after the shading correction in accordance with each eye point distance is performed on the eye images in FIGS. 6A and 6B respectively. Compared with the eye images in FIGS. 6A and 6B, the brightness unevenness has been suppressed in the eye images in FIGS. 7A and 7B, and the brightness unevenness of FIG. 7A and of FIG. 7B are approximately the same.

In a second method for suppressing the brightness unevenness, the CPU 3 changes the light-emitting amount (illumination light quantity) of the light sources 13a and 13b respectively in accordance with the eye point distance. For example, in the case where the eye point distance 500 is shorter than a predetermined distance, as in the case of FIG. 5A, the CPU 3 increases the light-emitting amount of the light source 13a to be relatively larger than the light-emitting amount of the light source 13b. In the case where the eye point distance is longer than a predetermined distance, as in the case of FIG. 5B, the CPU 3 decreases the light-emitting amount difference between the light source 13a and the light source 13b to be smaller than the light-emitting amount difference in FIG. 5A. With this second method as well, an effect similar to the first method is acquired. In the case where the light sources 13a and 13b are light-emitting diodes, the CPU 3 changes at least one of amplitude and duty ratio of the driving signal to drive the light source, for example, to adjust the light-emitting amount difference between the light sources.

Figure 8A:
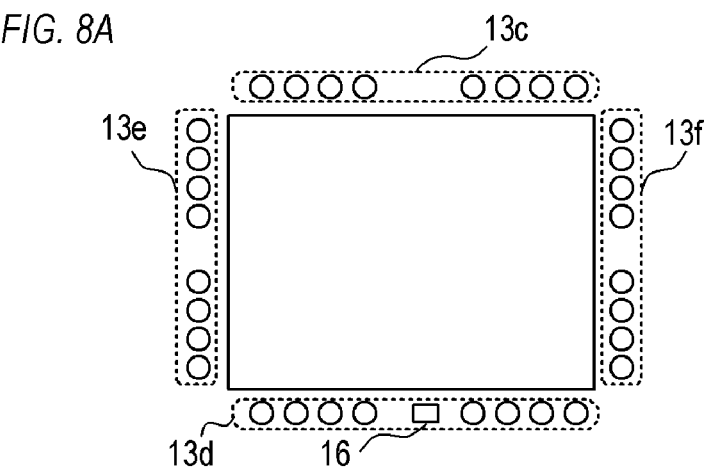
FIGS. 8A to 8C are diagrams indicating the disposition of a plurality of light sources according to Embodiment 1.
Figure 8B:
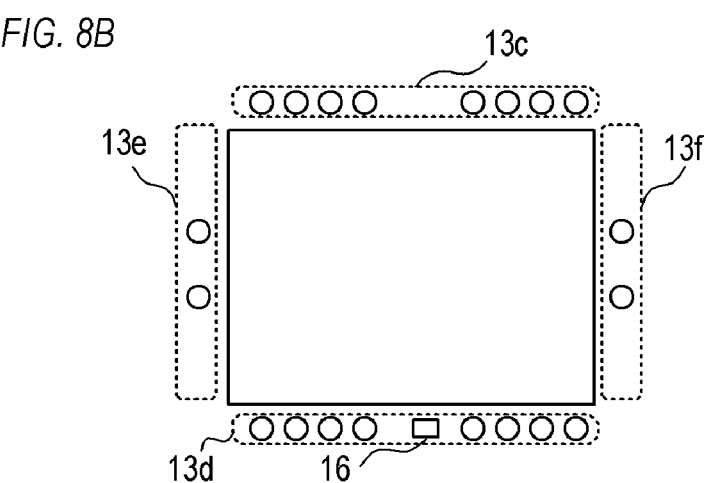
Figure 8C:
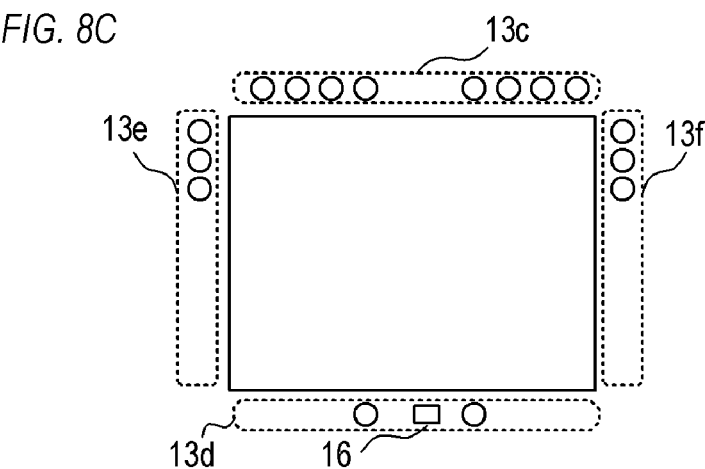

FIGS. 8A to 8C are diagrams indicating the disposition examples of a plurality of light sources. In the case where a plurality of light sources exist around the eyepiece, as indicated in FIGS. 8A to 8C, the CPU 3 may separate a plurality of light sources into a plurality of light source groups (four light source groups 13c to 13f in the case of FIGS. 8A to 8C), and adjust the light-emitting amount for each light source group. Each light source group includes one light source or two or more light sources located close to each other. The CPU 3 may adjust the light-emitting amount difference between the light source groups by changing the number of light sources that emit light (that are turned ON) in the respective light source group.

Further, the CPU 3 may suppress the brightness unevenness by combining the first method and the second method. The above is the description on the generation principle of the brightness unevenness of the eye image and suppression method.

Now the calibration operation, the image capturing operation and the line-of-sight detection operation according to Embodiment 1 will be described with reference to FIGS. 9 to 11.

Calibration Operation

Figure 9:
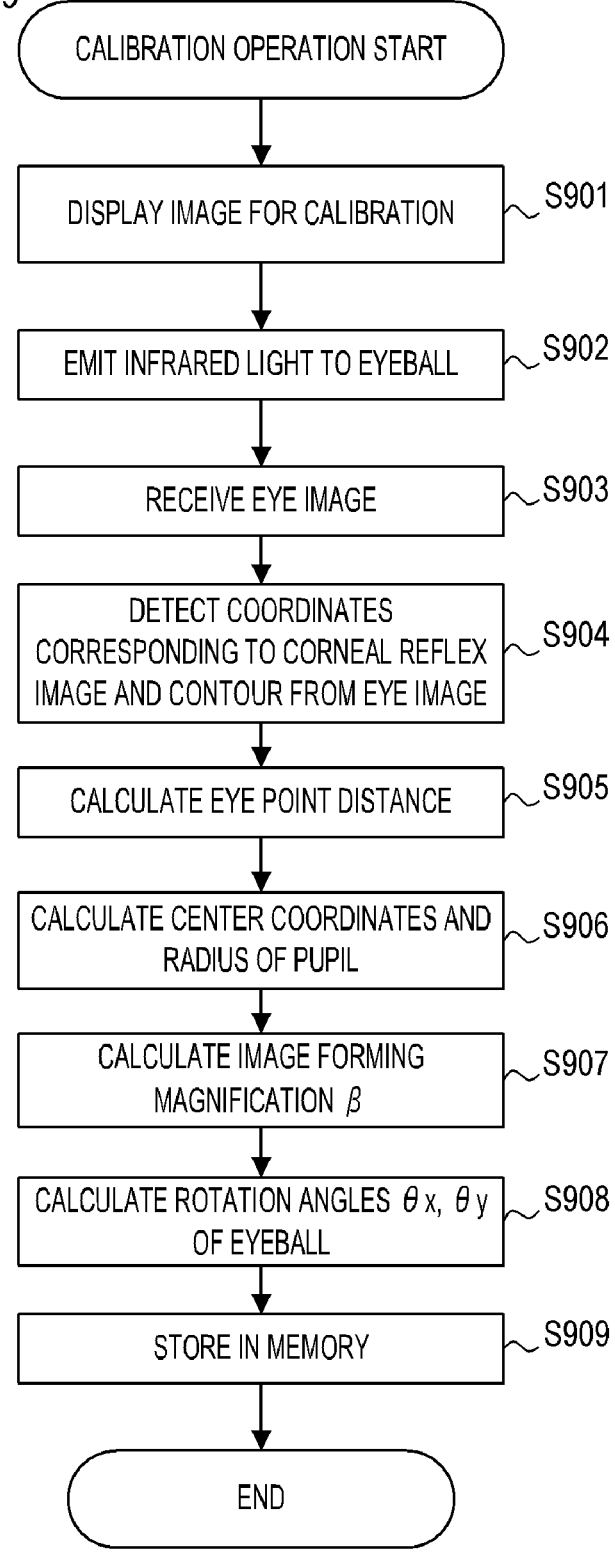
FIG. 9 is a flow chart of a calibration operation according to Embodiment 1.

FIG. 9 is a flow chart for describing the calibration operation for the line-of-sight detection.

In step S901, the CPU 3 displays an image used for calibration on the display device 10. The image used for calibration can be any image that indicates the position at which the user should look at on the display surface of the display device 10.

In step S902, the CPU 3 emits the infrared lights of the light sources 13a and 13b toward the eyeball 14 of the user. The eyeball image illuminated by the infrared light is formed on the eye image pickup element 16 via the light-receiving lens 15, and is photoelectrically converted by the eye image pickup element 16. Thereby the processable electric signal of the eye image can be acquired.

In step S903, the CPU 3 receives the eye image (eyeball image signal; electrical signal of the eye image) from the eye image pickup element 16.

In step S904, the CPU 3 determines the coordinates corresponding to the corneal reflex images Pd and Pe of the light sources 13a and 13b, and the coordinates corresponding to the contour of the pupil 141, from the eye image received in step S903.

In step S905, the CPU 3 acquires the distance information that indicates the distance from the eyepiece 12 to the eyeball 14 of the user (eye point distance). For example, the CPU 3 calculates the eye point distance from the distance between the corneal reflex images Pd and Pe of the eye image received in step S903. The eye point distance can be calculated using a known technique.

In step S906, the CPU 3 calculates the coordinates of the center c of the pupil 141 and the radius r thereof by the circle approximation method, using the contour coordinates of the pupil 141 determined in step S904.

In step S907, the CPU 3 calculates the image forming magnification β of the eyeball image. In step S908, the CPU 3 calculates the rotation angles θx and θy of the optical axis of the eyeball 14 with respect to the optical axis of the light-receiving lens 15.

In step S909, the CPU 3 stores the rotation angles θx and θy calculated in step S908 in the memory unit 4 as the correction values θx_cal and θy_cal. The CPU 3 also stores the eye point distance calculated in step S905 in the memory unit 4. In step S909, the CPU 3 may store the shading correction values (correction value used for shading correction, peripheral light quantity loss correction value) in accordance with the eye point distance, or light-emitting amount of a plurality of light sources (e.g. light sources 13a, 13b) in the memory unit 4. When the processing in step S909 ends, the CPU 3 ends the calibration operation for the line-of-sight detection.

Image Capturing Operation

After the calibration operation for the line-of-sight detection described in FIG. 9, the image capturing operation is performed. FIG. 10 is a flow chart for describing the image capturing operation of the camera 1 having the line-of-sight detection function. The CPU 3 starts the flow in FIG. 10 when the power of the camera 1 is turned ON.

In step S1001, the CPU 3 drives the image pickup element 2 and acquires (captures) the image. The CPU 3 displays the acquired image on the display device 10 (live view display; LV display).

In step S1002, the CPU 3 determines whether or not the image capturing operation ended. For example, the CPU 3 determines that the image capturing operation ended when an instruction to turn the power of the camera 1 OFF is received. The CPU 3 ends this processing flow if it is determined that the image capturing operation is ended, or advances the processing to step S1003 if not.

In step S1003, the CPU 3 performs the line-of-sight detection operation. The line-of-sight detection operation will be described in detail later with reference to the flow chart in FIG. 11.

In step S1004, the CPU 3 corrects the rotation angles θx and θy of the eyeball detected in step S1003. From the rotation angles θx and θy detected in step S1003 and the correction values θx_cal and θy_cal stored in step S909, the CPU 3 calculates the line-of-sight position (Hx, Hy).

In step S1005, the CPU 3 displays an auto focus (AF) frame at the line-of-sight position on the display device 10 calculated in step S1004.

In step S1006, the CPU 3 determines whether the switch SW1 is ON (whether the release button is half depressed). The CPU 3 advances the processing to step S1007 if the switch SW1 is ON, or returns the processing to step S1001 if not, and repeats displaying the image and performing the line-of sight detection operation.

In step S1007, the CPU 3 performs the AF operation. The image pickup element 2 is constituted of a plurality of pixels that are used for detecting the phase difference. Using the image plane phase difference AF (a known technique), the CPU 3 computes the focusing state of the object corresponding to the AF frame determined in step S1006, from the signals of the plurality of pixels, so as to control the lens position.

In step S1008, the CPU 3 determines whether the switch SW2 is turned ON by further depressing the release button (whether the release button was fully depressed). The CPU 3 advances the processing to step S1009 if the switch SW2 is turned ON, or returns the processing to step S1006 if not, and repeats the AF operation at the same position.

In step S1009, the CPU 3 drives the image pickup element 2 and acquires an image, and stores the acquired image in the storage medium (not illustrated). Then the CPU 3 returns the processing to step S1001 and repeats the processing.

Figure 10:
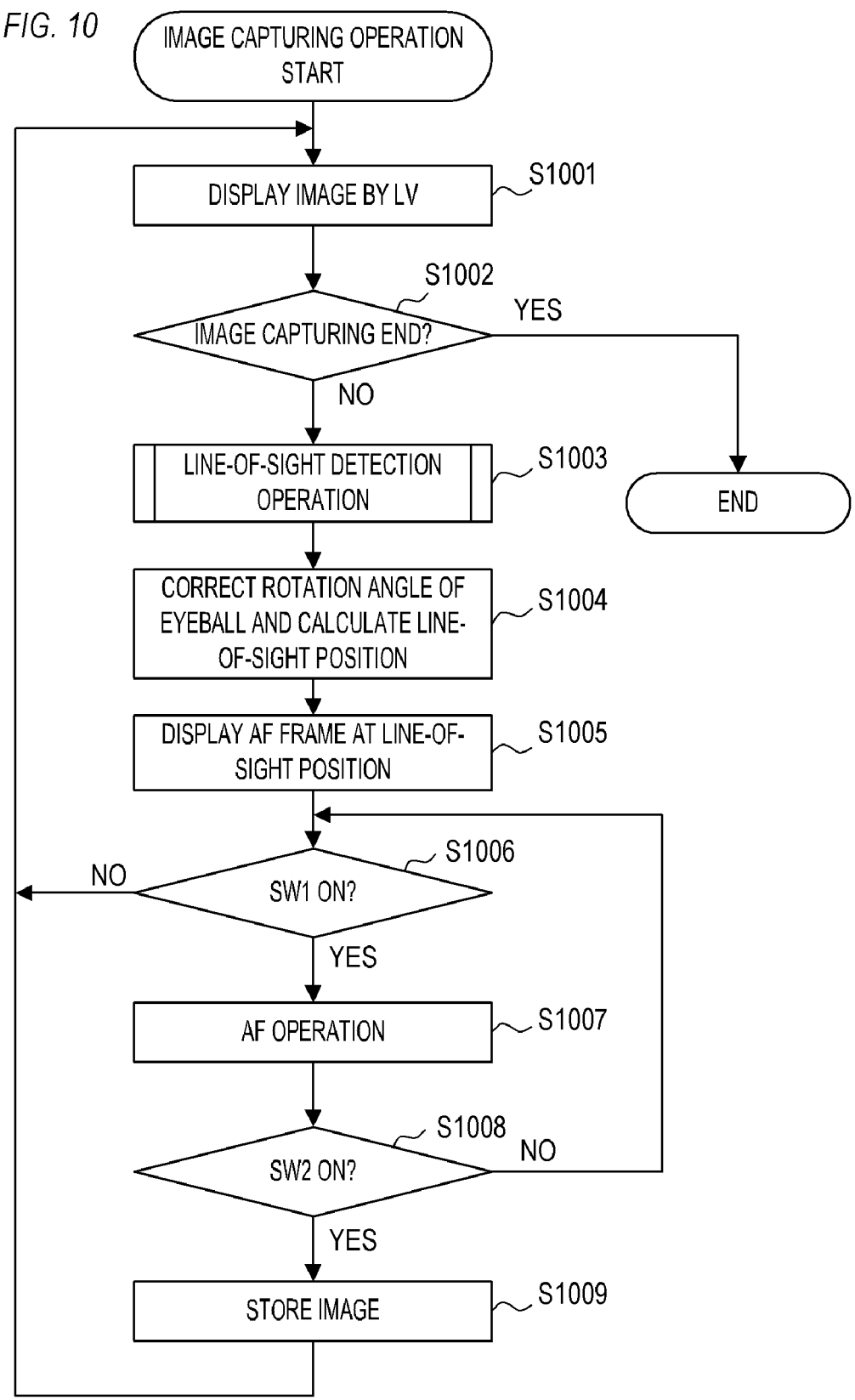
FIG. 10 is a flow chart of an image capturing operation according to Embodiment 1.
Figure 11:
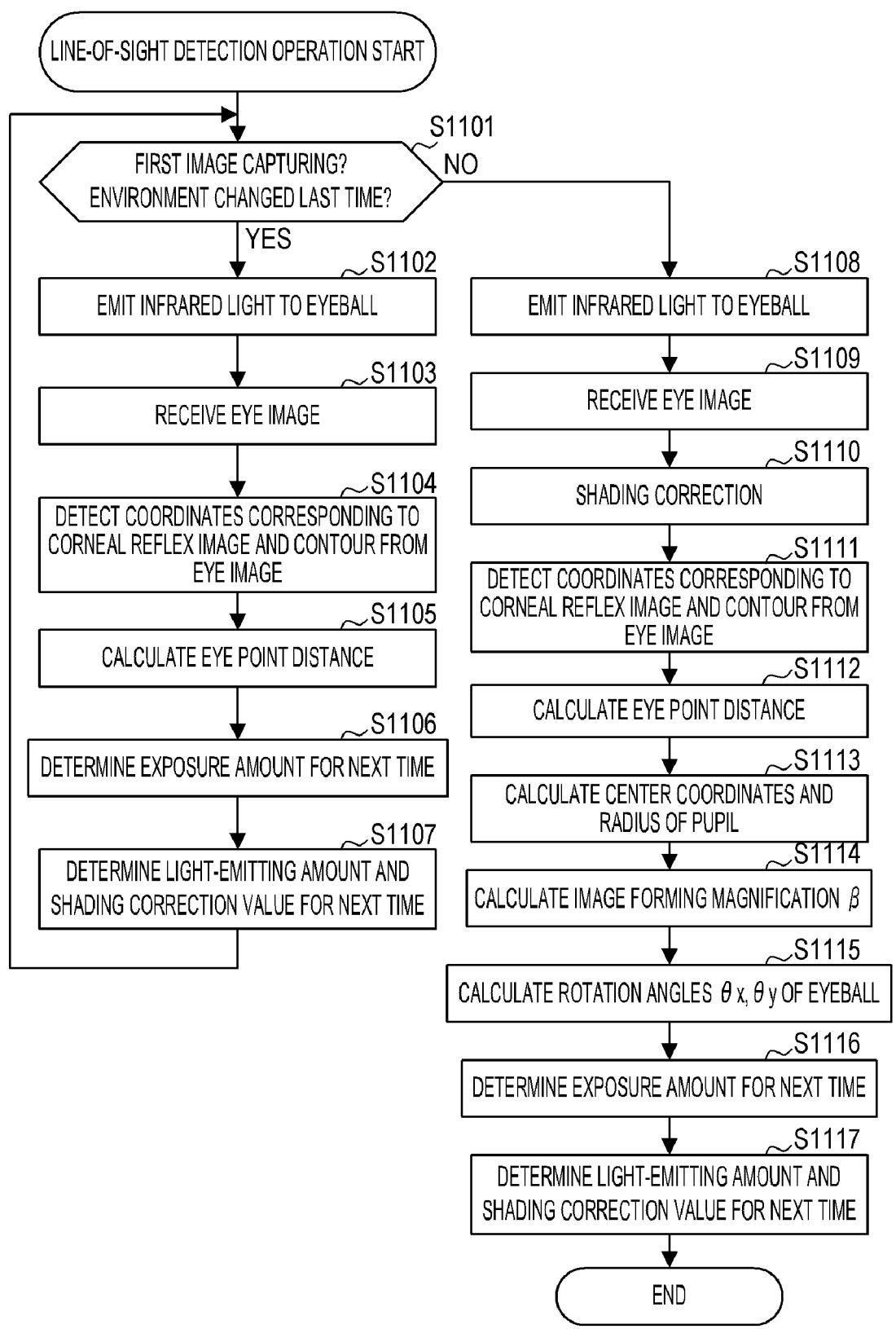
FIG. 11 is a flow chart of a line-of-sight detection operation according to Embodiment 1.

FIG. 11 is a flow chart indicating an example of the line-of-sight detection operation executed in step S1003 in FIG. 10 (line-of-sight detection operation during image capturing).

In step S1101, the CPU 3 determines: whether this is the first image capturing (whether the line-of-sight detection operation is performing for the first time); or a predetermined environmental change occurred in the previous image capturing; or that neither is applicable.

The CPU 3 advances the processing to step S1102 if this is the first image capturing or a predetermined environmental change has occurred, or advances the processing to step S1108 if not. The CPU 3 may determine that a predetermined environmental change has occurred, for example, in a case where the brightness of the eye image captured in the previous image capturing is not the brightness that is appropriate for detecting the corneal reflex images Pd and Pe and the contour coordinates (is not the brightness within the predetermined brightness range). For example, when the eye point distance suddenly becomes shorter than in the image capturing of two image capturing times ago, or when external light leaked in, a brightness change exceeding a predetermined amount is generated, and detection of the corneal reflex images Pd and Pe and the contour coordinates becomes difficult. Therefore the CPU 3 executes the processing in steps S1102 to S1107 again, in order to determine an appropriate exposure amount, illumination light quantity and shading correction value.

In steps S1102 to S1107, the CPU 3 detects (calculates) the eye point distance, and determines the exposure amount, the light-emitting amount and the shading correction value for the next image capturing. The processing in steps S1102 to S1105 is the same as the processing in steps S902 to S905 in FIG. 9.

In step S1102, the CPU 3 may set the light-emitting amount of the light source 13a to be similar to the light-emitting amount of the light source 13b. The CPU 3 may also determine the light-emitting amounts of the light source 13a and the light source 13b, so as to have a light-emitting amount difference appropriate for the exposure amount determination processing and the eye point distance detection processing. For example, the CPU 3 may determine the light-emitting amounts of the light source 13a and the light source 13b, so that the brightness unevenness of the eye image is suppressed with the eye point distance of which number of times of use is larger than a predetermined threshold. The CPU 3 may also set the light-emitting amounts of the light source 13a and the light source 13b to be light source amounts corresponding to an eye point distances stored in the memory unit 4 during the calibration operation (step S909).

In step S1106, the CPU 3 determines the exposure amount for the next image capturing (for the next charge storage of the image pickup element 16). For example, in step S1106, the CPU 3 determines the charge storage time or gain value of the eye image pickup element 16, so as to acquire an eye image capturing the contour of the pupil and the corneal reflex image at a desired brightness.

In step S1107, the CPU 3 determines the light-emitting amount and the shading correction value for the next image capturing in accordance with the eye point distance calculated in step S1105. Here the correspondence relationship between the eye point distances and the light-emitting amounts of a plurality of light sources, and the correspondence relationship between the eye point distances and the shading correction values are predetermined. By using the predetermined light-emitting amounts and the shading correction values, an eye image appropriate for the line-of-sight detection in accordance with the eye point distance can be quickly acquired, even if a plurality of light sources are disposed.

The light-emitting amounts of the plurality of light sources at each eye point distance will be described with reference to FIGS. 5A, 5B and 8A. With each eye point distance, the CPU 3 controls the plurality of light sources so as to emit light at the light-emitting amount based on the positional relationship between the plurality of light sources and the eye image pickup element 16. For example, it is assumed that the plurality of light sources are classified into a plurality of light source groups, each of which light-emitting amount can be controlled individually, including a light source group 13d (first light source; light source group) and a light source group 13c (second light source; light source group). The distance of the light source group 13c from the eye image pickup element 16 is longer than the distance of the light source group 13d from the eye image pickup element 16. In this case, the CPU 3 may set the light-emitting amount of the light source group 13c to be larger than the light-emitting amount of the light source group 13d. For example, the CPU 3 may turn ON a larger number of light sources in the light source group 13c than a number of light sources turned ON in the light source group 13d. The light sources may also be disposed such that a number of light sources included in the light source group 13c becomes larger than a number of light sources included in the light source group 13d. Thereby it can be suppressed that the region illuminated by the light source group 13c becomes darker than the region illuminated by the light source group 13d. In the case where the eye point distance is a first distance (FIG. 5A), the CPU 3 may increase the light-emitting amount difference between the light sources to be larger than the case where the eye point distance is a second distance which is longer than the first distance (FIG. 5B). Thereby the brightness unevenness can be more effectively suppressed, even in a case where the eye point distance is shorter than the predetermined distance and the brightness unevenness is likely to be generated.

It is preferable that a plurality of combinations of the eye point distances and the light-emitting amounts of the plurality of light sources are determined in advance.

In a case where the camera 1 further includes a third light source group (light source) of which distance from the eye image pickup element 16 is at least the distance from the eye image pickup element 16 to the second light source group (light source), the CPU 3 may set the light-emitting amount of the third light source group to be larger than the light-emitting amount of the second light source group. For example, in FIGS. 8A to 8C, the relationship of the distance from eye image pickup element 16 to each light source group is: distance to the light source group 13c>distance to the light source group 13e (13f)>distance to the light source group 13d. In the case of the example in FIG. 8A, the CPU 3 controls the light-emitting amount of each light source group to be: light-emitting amount of the light source group 13c>light-emitting amount of the light source group 13e (13f)>light-emitting amount of the light source group 13d. The CPU 3 may also control the light-emitting amount of a light source included in each light source group to be: light-emitting amount of a light source included in the light source group 13c>light-emitting amount of a light source included in the light source group 13e (13f)>light-emitting amount of a light source included in the light source group 13d. Here the relationship of the light-emitting amounts of the light sources may not satisfy the light-emitting amount of a light source included in the light source group 13c>light-emitting amount of a light source included in the light source group 13e (13f)>light-emitting amount of a light source included in the light source group 13d. In the same manner, the relationship of the light-emitting amounts of the light source groups may not satisfy the light-emitting amount of the light source group 13c>light emitting amount of the light source group 13e (13f)>light-emitting amount of the light source group 13d.

For example, the CPU 3 may not have to set the light-emitting amount of the third light source group to be larger than the light-emitting amount of the second light source group. The CPU 3 may control the light-emitting amount of each light source considering a number of light sources included in each light source group as well. In the case of the example in FIG. 8B, a number of light sources included in the light source group 13e (13f) is less than a number of light sources included in the light source group 13c. In the case of FIG. 8B, the CPU 3 may control the relationship of the light-emitting amount of each light source group to be: light-emitting amount of the light source group 13e (13f)>light-emitting amount of the light source group 13c>light-emitting amount of the light source group 13d. Further, the CPU 3 may control the relationship of the light-emitting amount of a light source included in each light source group to be: light-emitting amount of a light source included in the light source group 13e (13f)>light-emitting amount of a light source included in the light source group 13c>light-emitting amount of a light source included in the light source group 13d. Thereby it can be suppressed that the region illuminated by the light source group 13e becomes darker than the regions illuminated by the other light source groups.

Depending on the number of light sources included in each light source group, the light-emitting amount of the light source group, of which distance from the eye image pickup element 16 is shortest, may be set to be the shortest. In the case of the example in FIG. 8C, a number of light sources of the light source group 13d, which is a light source group of which distance from the eye image pickup element 16 is the shortest, is less than a number of light sources of the light source group 13c or 13e. In such a case as FIG. 8C, the CPU 3 may control the relationship of the light-emitting amount of each light source group to be: light-emitting amount of the light source group 13d>light-emitting amount of the light source group 13e (13f)>light-emitting amount of the light source group 13c. Further, the CPU 3 may control the relationship of the light-emitting amount of a light source included in each light source group to be: light-emitting amount of a light source included in the light source group 13d>light-emitting amount of a light source included in the light source group 13e (13f)>light-emitting amount of a light source included in the light source group 13c. Thereby it can be suppressed that the region illuminated by the light source group 13d becomes darker than the regions illuminated by the other light source groups. Thus the CPU 3 can suppress the brightness unevenness by controlling the light-emitting amount of each light source, considering a distance from the eye image pickup element 16 to each light source, or a number of light sources included in each light source group. In the examples in FIGS. 8A to 8C, the light source groups 13c to 13f were described, but at least one of the light source groups may be a light source instead of a light source group.

The shading correction value in each eye point distance will be described with reference to FIGS. 5A and 5B. In the case where the eye point distance is the first distance (FIG. 5A), the CPU 3 may increase the correction amount to be larger than that of the case of the second distance which is longer than the first distance (FIG. 5B). For example, in the case where the eye point distance is the first distance, the correction amount for an image region (a part of the eye image) corresponding to the region illuminated by the light source group 13c (a part of the eyeball) is increased to be larger than the correction amount for the image region corresponding to the region illuminated by the light source group 13d, compared with the case where the eye point distance is the second distance. It is preferable to predetermine such combinations of eye point distances and shading correction values.

For example, the light-emitting amounts of the light source 13a and the light source 13b and the shading correction value are stored in the memory unit 4 for each eye point distance. From the memory unit 4, the CPU 3 reads the light-emitting amount and the shading correction value corresponding to the eye point distance calculated in step S1105, and uses these values for the next computing (image capturing). In a case where the eye point distance calculated in step S1105 is a distance between eye point distances stored in the memory unit 4, the CPU 3 may perform interpolation processing. In other words, if a combination of the eye point distance and the light-emitting amount or the shading correction value is not predetermined for the eye point distance calculated in step S1105, the CPU 3 performs interpolation processing. For example, the CPU 3 acquires the light-emitting amount corresponding to the calculated eye point distance by the interpolation processing, using a plurality of combinations of the eye point distances close to the calculated eye point distance, out of the eye point distances stored in the memory unit 4, and the light-emitting amounts thereof. The interpolation processing for the shading correction values is also performed in the same manner. The CPU 3 may also store the light-emitting amount and the shading correction value corresponding to the eye point distance in the memory unit 4 in advance during calibration operation (step S909). In step S1107, from the memory unit 4, the CPU 3 may read the light-emitting amount and the shading correction value corresponding to the eye point distance stored during calibration. Further, the CPU 3 may determine the light-emitting amount or the shading correction value by referring to the information stored in an external storage medium, instead of the memory unit 4.

As a consequence, when the image capturing is performed for the first time, or when a predetermined environmental change occurred in the initial image capturing or in previous image capturing, the next image capturing can be performed without correcting the brightness unevenness of the eye image, whereby the exposure condition can be quickly determined, and the eye point distance, pupil, and the like can be detected.

In step S1108, the CPU 3 emits the infrared lights from the light sources 13a and 13b to the eyeball 14 of the user at the light-emitting amount determined in step S1107 or step S1117.

In step S1110, the CPU 3 performs shading correction on the eye image acquired in step S1109, using the correction value determined in step S1107 or step S1117.

The processing in steps S1109 and S1111 to S1115 is the same as the processing in steps S903 to S908 in FIG. 9. The processing step S1116 is the same as the processing in step S1106.

In step S1117, the CPU 3 determines the light-emitting amount and the shading correction value for the next image capturing in the same manner as the processing in step S1107 in accordance with the eye point distance calculated in step S1112. The CPU 3 ends the line-of-sight detection operation at image capturing when the processing in step S1117 ends.

In a case where the plurality of light sources are light-emitting diodes and the light-emitting amounts disperse depending on the light-emitting diode, the CPU 3 may control (adjust) the light-emitting amounts of the plurality of light sources considering the light-emitting efficiency of each of the plurality of light sources. By considering the light-emitting efficiency, the CPU 3 can implement light emission at the light-emitting amounts stored in the memory unit 4 at high precision. Therefore the brightness unevenness can be suppressed at high precision. The brightness unevenness with each eye point distance may be measured for each individual line-of-sight detection apparatus, and the light-emitting amounts and the shading correction values, to suppress the brightness unevenness, may be stored in the memory unit 4.

In the case of the example in FIG. 11, the CPU 3 does not perform the processing for calculating the center coordinates of the pupil and the like (processing in steps S1113 to S1115) when the image capturing is performed for the first time, or when a predetermined environmental change occurred in the previous image capturing, but this processing of calculating the center coordinates of the pupil and the like may be performed. For example, the CPU 3 may determine the light-emitting amounts of the light source 13a and the light source 13b such that the brightness unevenness of the eye image is suppressed with an eye point distance of which frequency of use is larger than a predetermined threshold, and perform the processing for calculating the center coordinates of the pupil and the like using the eye image captured at the light-emitting amounts.

As described above, in Embodiment 1, the CPU 3 changes the light-emitting amounts of the light sources and performs the shading correction in accordance with the eye point distance. Thereby the brightness unevenness of the captured eye image can be suppressed.

Embodiment 2

In Embodiment 1, the CPU 3 performs both changing the light-emitting amounts of the light sources and the shading correction in accordance with the eye point distance. The CPU 3 may also perform only one of the control of the light-emitting amounts of the light sources and the shading correction, in accordance with the eye point distance. In Embodiment 2, an example where the CPU 3 performs the shading correction in accordance with the eye point distance will be described. A difference of Embodiment 2 from Embodiment 1 is that the light-emitting amounts of the light sources are not changed in accordance with the eye point distance.

Figure 12:
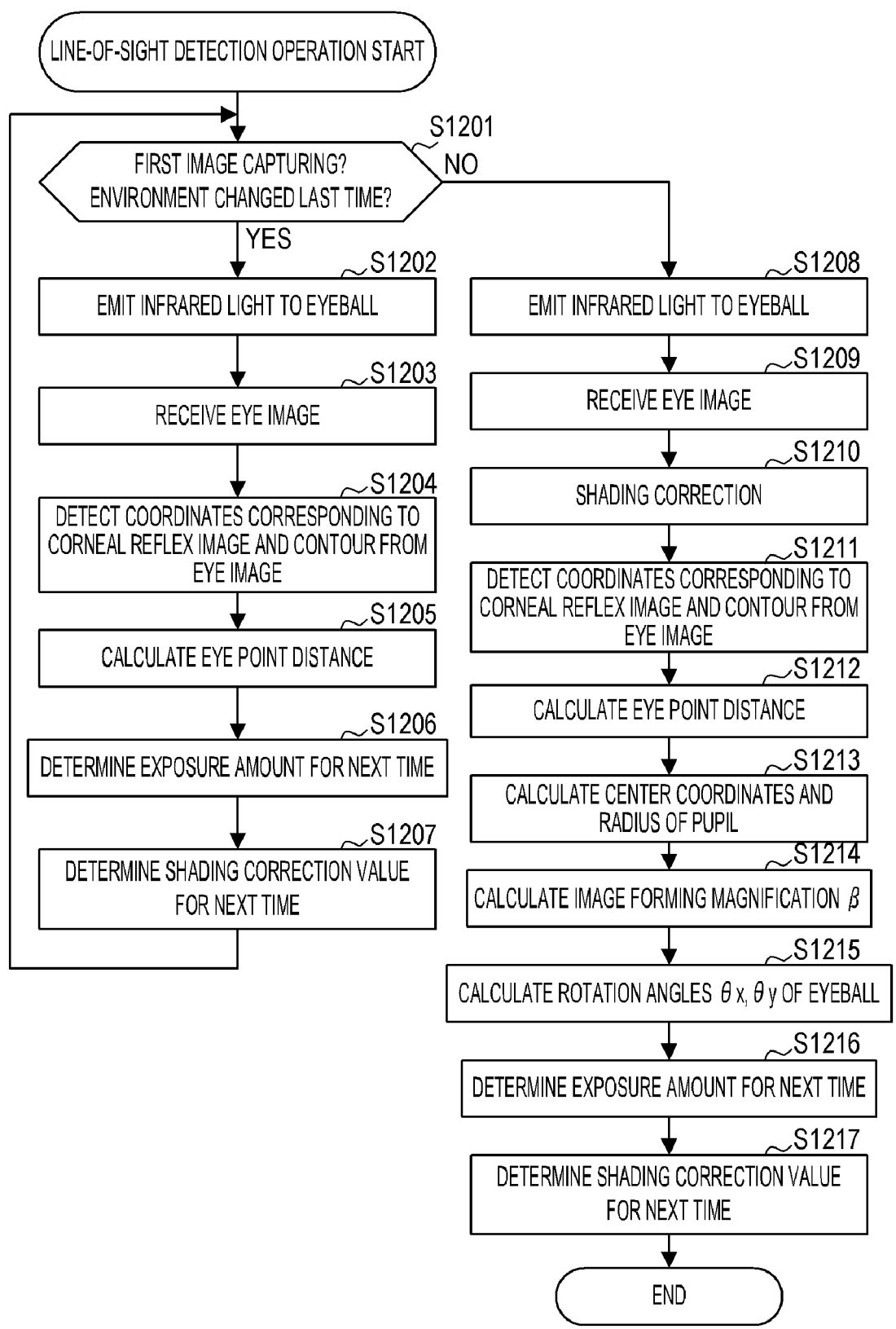
FIG. 12 is a flow chart of a line-of-sight detection operation according to Embodiment 2.

FIG. 12 is a flow chart for describing an example of the line-of-sight detection operation executed in step S1003 in FIG. 10. The processing in steps S1201 to S1206 and S1209 to S1216 are the same as the processing in steps S1101 to S1106 and S1109 to S1116 in FIG. 11.

In step S1207, the CPU 3 determines the shading correction value for the next image capturing in accordance with the eye point distance calculated in step S1205.

In step S1208, the CPU 3 emits infrared lights from the light sources 13a and 13b to the eyeball 14 of the user. The processing in step S1208 may be the same as the processing in step S1102 (S1202). For example, the CPU 3 may emit the infrared lights from the light sources 13a and 13b to the eyeball 14 of the user at the light-emitting amounts with which the brightness unevenness of the eye image is suppressed with an eye point distance, of which frequency of use is higher than a predetermined threshold. Thus in Embodiment 2, the CPU 3 does not change the light-emitting amounts of the light sources in accordance with the eye point distance, but uses fixed values.

In step S1217, the CPU 3 determines the shading correction value for the next image capturing in accordance with the eye point distance calculated in step S1212.

As described above, in Embodiment 2, the CPU 3 uses fixed values for the light-emitting amounts of the light sources, and determines the shading correction value in accordance with the eye point distance. Thereby the brightness unevenness of the eye image can be suppressed using processing simpler than Embodiment 1.

Embodiment 3

In Embodiment 3, an example in which the CPU 3 changes the light-emitting amounts of the light sources in accordance with the eye point distance will be described. A difference of Embodiment 3 from embodiment 1 is that the shading correction is not performed.

Figure 13:
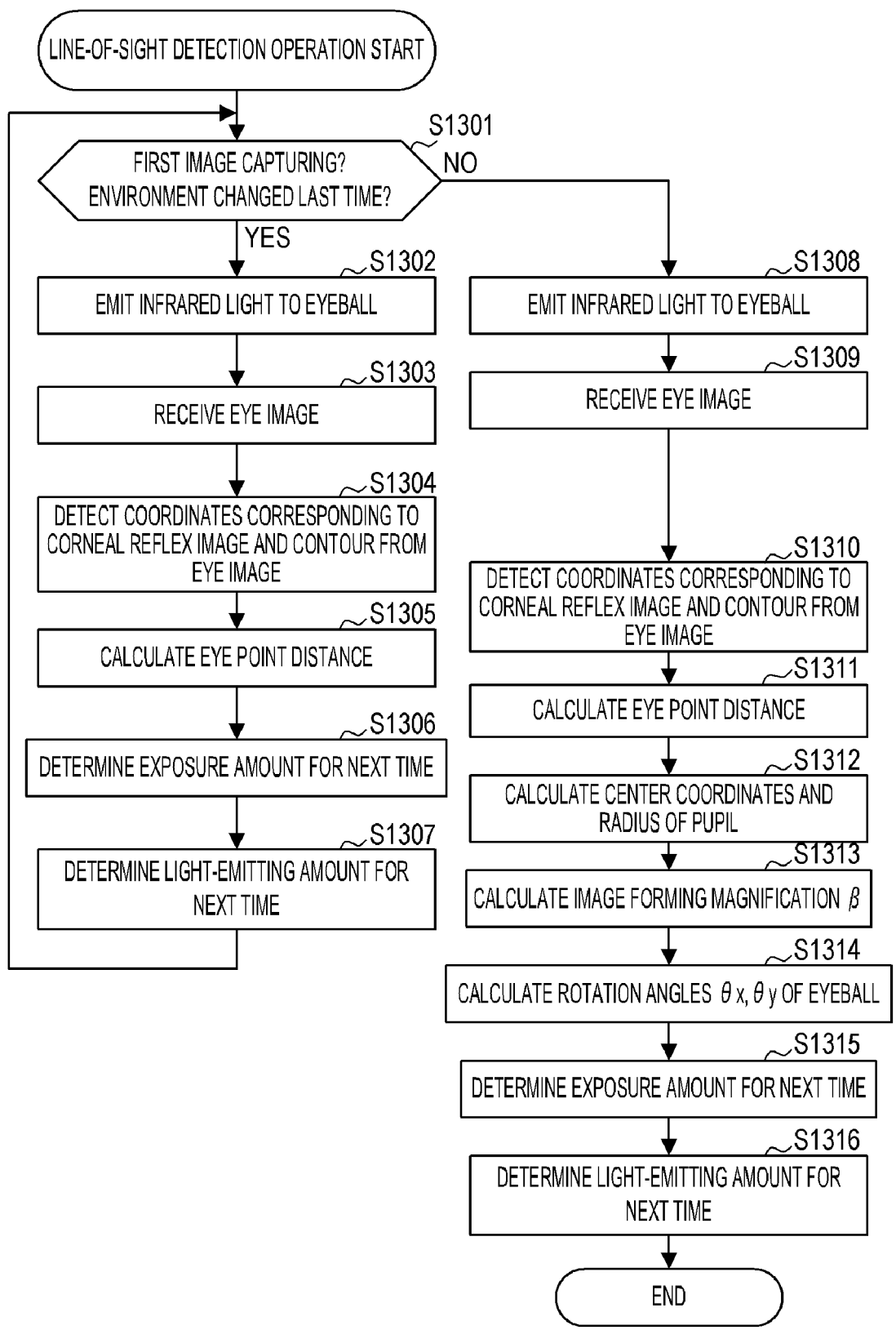
FIG. 13 is a flow chart of a line-of-sight detection operation according to Embodiment 3.

FIG. 13 is a flow chart for describing an example of the line-of-sight detection operation executed in steps S1003 in FIG. 10. The processing in steps S1301 to S1306 and S1308 to S1315 are the same as the processing in steps S1101 to S1106, S1108, S1109 and S1111 to S1116 in FIG. 11.

In step S1307, the CPU 3 determines the light-emitting amounts for the next image capturing in accordance with the eye point distance calculated in step S1305.

In step S1316, the CPU 3 determines the light-emitting amounts from the next image capturing in accordance with the eye point distance calculated in step S1311.

As described above, in Embodiment 3, the CPU 3 does not perform the shading correction, and changes the light-emitting amounts of the light sources in accordance with the eye point distance. Thereby the brightness unevenness of the eye image can be suppressed using processing simpler than Embodiment 1.

Embodiment 4

In Embodiments 1 to 3, examples of applying the present invention to the camera 1 were described, but the present invention is also applicable to a head mounted display (HMD), for example. An example of applying the present invention to an HMD will be described next.

Figure 14A:
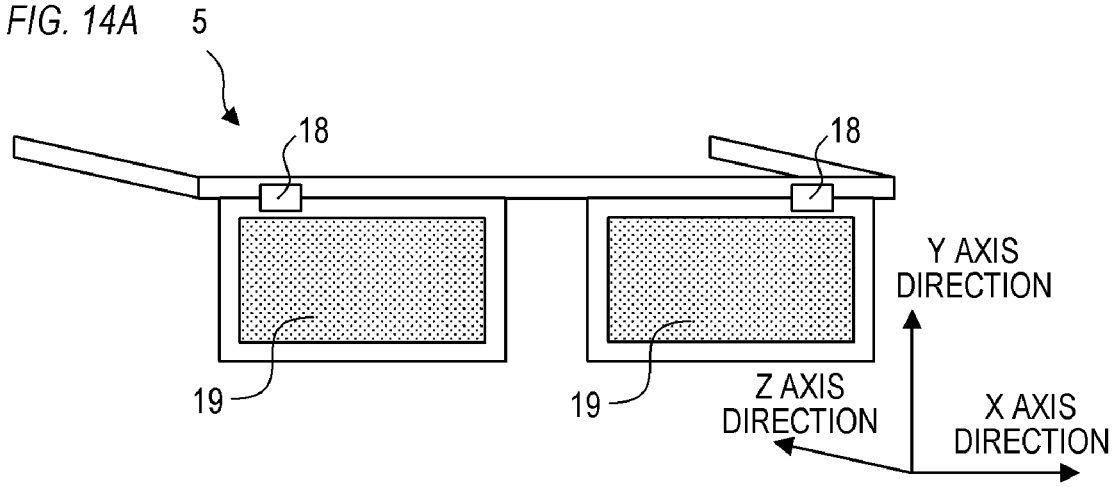
FIGS. 14A and 14B are external views of a display apparatus according to Embodiment 4.
Figure 14B:
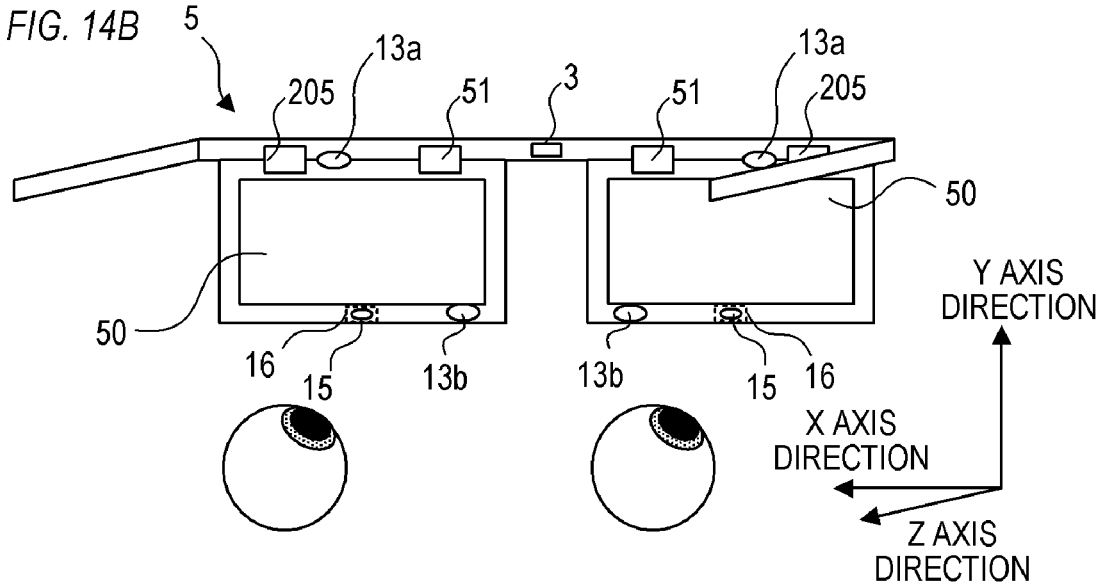

FIGS. 14A and 14B are external views of a display apparatus 5 according to Embodiment 4. FIG. 14A is a front perspective view, and FIG. 14B is a rear perspective view. The display apparatus 5 is an optical see through type display apparatus, and is a type of HMD which is wearable on the head. The display apparatus 5 is a spectacle device that uses mixed reality (MR) or augmented reality (AR). The display apparatus 5 can detect the line-of-sight of the right eye, and the line-of-sight of the left eye of the user individually, who is wearing the display apparatus 5 on their head.

A lens 50 is an optical member facing the eye of the user. The user can visually recognize the external world through the lens 50. Based on control (display control) by the CPU 3 which controls the entire display apparatus 5, the display device 51 displays a virtual object (virtual image of the virtual object) for both eyes (both the right eye and left eye) of the user. The user can view the displayed virtual object as if the object existed in the external world. The light source driving circuit 205 drives the light sources 13a and 13b. Each of the light sources 13a and 13b is a light source to illuminate the eye of the user, and is an infrared light-emitting diode, for example, which emits infrared light that is invisible to the user. A part of the lights emitted from the light sources 13a and 13b and reflected by the eye of the user is collected on the eye image pickup element 16 via the light-receiving lens 15. These members are disposed for the left eye and the right eye respectively. For example, for the eye image pickup element 16, a right image pickup element which images the right eye and a left image pickup element which images the left eye are disposed. In the example in FIG. 14B, one light source 13a and one light source 13b are disposed at the top and bottom of the lens 50, for the left eye and the right eye respectively, but two or more light sources may be disposed, and the light sources may be disposed at the left and right of the lens 50. A light control device 19 (light control panel) adjusts light from the outside. A light control circuit 18 is a circuit to change the transmittance of the light control device 19, and is a circuit to control the voltage applied to the light control device 19, for example. The light control device 19 transmits the light from the external world at the transmittance controlled by the light control circuit 18.

The user positions the display apparatus 5 on their nose to use it, hence the eye point distance is approximately constant regardless the user. Hence the CPU 3 controls the light-emitting amounts or performs shading correction such that the brightness unevenness of the eye image with a specific eye point distance (e.g. average eye point distance when the user uses the display apparatus 5 positioned on their nose). For example, the CPU 3 controls a plurality of light sources so that the lights are emitted at light-emitting amounts based on the positional relationship between the plurality of light sources and the eye image pickup element 16. The CPU 3 also performs the shading correction so that the brightness unevenness with a specific eye point distance is suppressed.

As described above, in Embodiment 4, the CPU 3 can suppress the brightness unevenness of the eye image of the user using the HMD.

According to the present invention, the brightness unevenness of the captured image of the eyeball can be suppressed.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2022-069647, filed on Apr. 20, 2022, which is hereby incorporated by reference herein in its entirety.

What is claimed is:

1. An electronic apparatus comprising:
a plurality of light sources configured to illuminate an eyeball;
an image sensor configured to capture the eyeball illuminated by the plurality of light sources; and
at least one memory and at least one processor which function as a control unit configured to control the plurality of light sources, wherein
the control unit controls the plurality of light sources so as to emit light at a light-emitting amount based on a positional relationship between each of the plurality of light sources and the image sensor, wherein
the plurality of light sources include a first light source, and a second light source of which a distance from the image sensor is longer than a distance from the image sensor to the first light source, and
the control unit increases a light-emitting amount of the second light source to be larger than a light-emitting amount of the first light source.

2. The electronic apparatus according to claim 1, wherein for each of the plurality of light sources, the control unit controls at least one of amplitude and a duty ratio of a driving signal to drive the light source.

3. The electronic apparatus according to claim 1, wherein the plurality of light sources are classified into a plurality of light source groups each of which light-emitting amount is controllable individually, including a first light source group, and a second light source group of which a distance from the image sensor is longer than a distance from the image sensor to the first light source group, and
the control unit increases a light-emitting amount of the second light source group to be larger than a light-emitting amount of the first light source group.

4. The electronic apparatus according to claim 3, wherein the plurality of light source groups further includes a third light source group of which a distance from the image sensor is at least the distance from the image sensor to the second light source group,
a number of light sources included in the second light source group is less than a number of light sources included in the third light source group, and
the control unit does not increase a light-emitting amount of the third light source group to be larger than the light-emitting amount of the second light source group.

5. The electronic apparatus according to claim 3, wherein for each of the plurality of light source groups, the control unit controls at least one of: an amplitude of a driving signal to drive the light source group; a duty ratio of the driving signal; and a number of light sources that are turned ON in the light source group.

6. The electronic apparatus according to claim 1, wherein
the at least one memory and the at least one processor further function as a second acquisition unit configured to acquire distance information that indicates a distance from the eyeball to the image sensor,
a correspondence relationship between a distance from the eyeball to the image sensor and a light-emitting amount of the plurality of light sources is predetermined, and
the control unit controls the plurality of light sources so as to emit light at the light-emitting amount of the plurality of light sources corresponding to the distance indicated by the distance information.

7. The electronic apparatus according to claim 6, wherein
the plurality of light sources are classified into a plurality of light source groups each of which light-emitting amount is controllable individually, including a first light source group, and a second light source group of which a distance from the image sensor is longer than a distance from the image sensor to the first light source group, and
in a case where the distance indicated by the distance information is shorter than a predetermined distance, the control unit increases the light-emission amount of the second light source group to be relatively larger than the light-emission amount of the first light source group.

8. The electronic apparatus according to claim 6, wherein
the plurality of light sources are classified into a plurality of light source groups each of which light-emitting amount is controllable individually, including a first light source group, and a second light source group of which a distance from the image sensor is longer than a distance from the image sensor to the first light source group, and
in a case where the distance indicated by the distance information is longer than a predetermined distance, the control unit decreases a light-emitting amount difference between the first light source group and the second light source group to be smaller than a light-emitting amount difference in a case where the distance indicated by the distance information is shorter than the predetermined distance.

9. The electronic apparatus according to claim 1, wherein
the control unit controls the plurality of light sources considering light-emitting efficiency of each of the plurality of light sources.

10. The electronic apparatus according to claim 1, wherein
the at least one memory and the at least one processor further function as:
a first acquisition unit configured to acquire an image of the eyeball captured by the image sensor; and
a detection unit configured to detect a gaze position using the image.

11. A control method of an electronic apparatus, comprising:
capturing an eyeball illuminated by a plurality of light sources with an image sensor; and
controlling the plurality of light sources, wherein
the plurality of light sources are controlled so as to emit light at a light-emitting amount based on a positional relationship between each of the plurality of light sources and the image sensor, wherein
the plurality of light sources include a first light source, and a second light source of which a distance from the image sensor is longer than a distance from the image sensor to the first light source, and
a light-emitting amount of the second light source is increased to be larger than a light-emitting amount of the first light source.

12. A non-transitory computer readable medium that stores a program, wherein the program causes a computer to execute the control method according to claim 11.

* * * * *